United States Patent [19]

Arlt

[11] Patent Number: 5,136,114
[45] Date of Patent: Aug. 4, 1992

[54] PROCESS FOR THE PREPARATION OF GEMINAL DIARYLALKANES, NEW GEMINAL DIARYLALKANES AND ALK(EN)YLATED AROMATIC COMPOUNDS

[75] Inventor: Dieter Arlt, Cologne, Fed. Rep. of Germany

[73] Assignee: Bayer Aktiengesellschaft, Leverkusen, Fed. Rep. of Germany

[21] Appl. No.: 516,629

[22] Filed: Apr. 30, 1990

[30] Foreign Application Priority Data

May 20, 1989 [DE] Fed. Rep. of Germany ....... 3916557

[51] Int. Cl.$^5$ ............... C07C 17/00; C07C 25/18; C07C 39/12; C07C 321/24
[52] U.S. Cl. .................. 570/192; 568/25; 568/68; 568/584; 568/588; 568/632; 568/715; 568/717; 568/722; 568/729; 568/808; 568/809; 568/812; 570/191; 570/194; 585/320; 585/323; 585/422; 585/438
[58] Field of Search ............ 570/191, 194, 192; 568/25, 68, 584, 588, 632, 715, 717, 720, 722, 729, 808, 809, 812; 585/320, 323, 422, 438

[56] References Cited

U.S. PATENT DOCUMENTS

| | | | |
|---|---|---|---|
| 2,308,419 | 1/1943 | Heitz | 570/194 |
| 2,355,850 | 8/1944 | Dreisbach | 570/194 |
| 2,485,017 | 10/1949 | Schmerling | 570/194 |
| 2,631,172 | 3/1953 | Schmerling | 570/194 |
| 2,654,791 | 10/1953 | Weston | 570/194 |
| 3,631,211 | 12/1971 | Schmerling | |
| 3,875,249 | 4/1975 | Nelson | 570/194 |
| 4,251,675 | 2/1981 | Engel | |
| 4,365,103 | 12/1982 | Chang et al. | |

OTHER PUBLICATIONS

The Journal of Organic Chemistry, May 1961, vol. 26, No. 5, pp. 1398–1401.
The Journal of Organic Chemistry, May 14, 1976, vol. 41, No. 10, pp. 1698–1701.

*Primary Examiner*—Werren B. Lone
*Attorney, Agent, or Firm*—Sprung Horn Kramer & Woods

[57] ABSTRACT

The invention relates to a new process for the preparation of geminal diarylalkanes of the formula

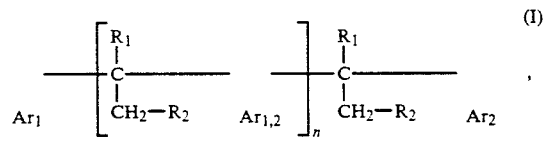

by Friedel-Crafts alkylation of aromatic compounds with specific aliphatic halogen compounds (addition compounds of $CCl_4$, to α-olefins), to new geminal diarylalkanes and the aralkyl compounds resulting as intermediates.

5 Claims, No Drawings

PROCESS FOR THE PREPARATION OF GEMINAL DIARYLALKANES, NEW GEMINAL DIARYLALKANES AND ALK(EN)YLATED AROMATIC COMPOUNDS

The invention relates to a new process for the preparation of geminal diarylalkanes, to new geminal diarylalkanes and to new alk(en)ylated aromatic compounds.

1,1-Diarylalkanes are easily obtainable by acid-catalyzed alkylation of aromatic compounds with aldehydes or styrenes (see, for example, J. Org. Chem. 26 (1961) p. 1398). The preparation of geminal diarylalkanes with non-terminal geminal aryl groups, which could be carried out, in principle, by condensation of aliphatic ketones or α-methylstyrenes with aromatic compounds, is limited, however, to the use of activated aromatic compounds such as phenols and anilines. Toluene, for example, cannot be condensed with acetone or methylstyrenes to give the corresponding 2,2-diarylpropanes (see J. Org. Chem. loc. cit.).

The preparation of geminal diarylalkanes with non-terminal aryl groups, for example 2,2-ditolylpropane, causes considerable difficulties and requires special alkylating agents and Friedel-Crafts catalysts in each case for each aromatic compound (see J. Org. Chem. loc. cit. and J. Org. Chem. 41 (1976) p. 1698 ff., in particular p. 1701).

As geminal diarylalkanes, especially also those with non-terminal aryl groups, have a considerable industrial interest as starting compounds, inter alia for the preparation of plastics (for example polyimides), the object was therefore to find an economical process by which geminal diarylalkanes could be prepared from all sorts of aromatic compounds.

Surprisingly, it has been found that certain 1,1,1,3-tetrachloropropanes or the isomeric 1,1,1-trichloro-2- or 1,1,3-trichloro-1-propenes obtainable from these by HCl elimination represent ideal aliphatic condensation components for aromatic compounds, as, per mole, they react with 2 moles of all sorts of aromatic compounds, activated or non-activated, in the presence of customary Friedel-Crafts catalysts with elimination of vinylidene chloride to give geminal diarylalkanes. Surprisingly, the Friedel-Crafts reaction of tetrachloropropanes (trichloropropenes) does not stop at the stage of the aralkyl compounds, but these aralkyl compounds react with further aromatic compound with the elimination of vinylidene chloride to give the desired geminal diarylalkanes.

This reaction of the tetrachloropropanes or trichloropropenes to be used according to the invention with aromatic compounds to give diarylalkanes has the advantage compared to the known processes that it is widely applicable, i.e. to all sorts of aromatic compounds, and the preparation of geminal diarylalkanes, which were hitherto not accessible at all or only in laboratory amounts, is made possible in industrial amounts, that it only requires customary Friedel-Crafts catalysts and that the halogenoalkanes or halogenoalkenes to be used as alkylating agents are obtainable by addition of $CCl_4$ to basic petrochemicals, namely α-olefins such as propene, i-butene, 2-methyl-1-butene, 2-methyl-1-pentene, 4-methyl-1-pentene, n-octene, n-dodecene, n-heptadecene and n-octadecene and are therefore easily accessible. $CCl_4$ is produced in a substantial amount as a chlorolysis product since organic chlorine-containing residues are customarily worked up by chlorolysis and new areas of use for $CCl_4$ are therefore sought.

The process according to the invention indicates an efficient route to convert this $CCl_4$, which can be prepared from waste products in a large amount, on the one hand into the desired geminal diarylalkanes but also on the other hand into the vinylidene chloride obtained as the coupling product; vinylidene chloride is a monomer which is in demand for the preparation of useful copolymers (for example modacrylic fibres, saran polymers).

That is to say, in the course of the newly found reaction, a conversion of the $CCl_4$ obtained during the residual chlorolysis (i.e., a $C_1$-compound with limited utility) takes place to give a $C_2$-compound having substantially wider utility (vinylidene chloride) as a result of the use of the halogenoalkanes or halogenoalkenes prepared from $CCl_4$ and olefins and their reaction with aromatic compounds to give diarylalkanes and vinylidene chloride.

The invention therefore relates to a process for the preparation of monomeric or oligomeric geminal diarylalkanes of the formula

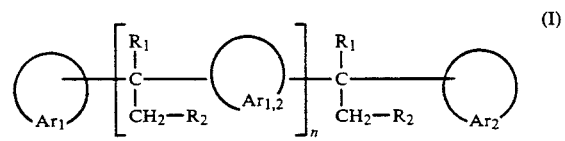 (I)

in which n is an integer from 1 to 5 or, preferably, zero,

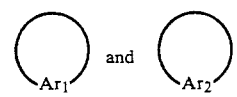

independently of one another represent an optionally substituted aryl radical and

either denotes a

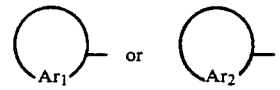

radical, $R_1$ represents hydrogen or a $C_1$–$C_{18}$-alkyl radical and $R_2$ represents hydrogen or an optionally substituted $C_1$–$C_{18}$-alkyl radical, which is characterized in that aromatic compounds of the formulae

 (II)

in which

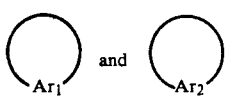

have the meaning indicated under formula (I), are reacted with an aliphatic halogen compound of the formulae

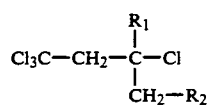  (IIIa)

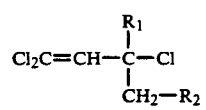  (IIIb)

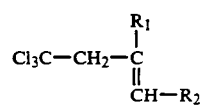  (IIIc)

in which $R_1$ and $R_2$ have the meaning indicated under formula (I), in the presence of Friedel-Crafts catalysts.

The molar ratios in which the aromatic compounds II and the aliphatic halogen compounds III are employed depends on the desired final products, and whether monomeric or oligomeric diarylalkanes are desired. For the preparation of monomeric geminal diarylalkanes (compounds of the formula (I) in which n is zero), the aromatic compounds II are employed in excess, preferably in an amount of 10 to 30 moles per mole of aliphatic halogen compound. For the preparation of the oligomeric geminal diarylalkanes (compounds of the formula (I) in which n is an integer from 1 to 5), the aromatic compounds and aliphatic halogenoalkanes are used, depending on the degree of oligomerization desired, in a molar ratio of 1:1 to 5:1.

The process according to the invention can be carried out both in the liquid phase and in the gas phase. When carrying out the process in the liquid phase, it is preferably carried out at temperatures of −50° to +200° C., preferably −20° to +150° C. Friedel-Crafts catalysts employed are the Friedel-Crafts catalysts customarily used for the alkylation of aromatic compounds, for example $AlCl_3$, $BF_3$, $FeCl_3$, $ZnCl_2$, $TiCl_4$, $ZrCl_4$, $SnCl_4$, $H_3PO_4$, HF, $HBF_4$, acidic alkaline earth phosphates, aluminas, zeolites or acidic ion exchange resins. If appropriate, the additional use of co-catalysts, as are frequently used in the Friedel-Crafts alkylation, may be advantageous for the acceleration of the reaction; a co-catalyst of this type is, for example, HCl.

The liquid phase alkylation according to the invention can be carried out, for example, as follows: one of the halogenoalkanes of the formula (IIIa–c), a mixture of these compounds or a solution of the compounds in an organic solvent is added with stirring at temperatures of −10° to +50° C. to the solution of the Friedel-Crafts catalyst in excess aromatic compound or in the aromatic compound diluted with an inert organic solvent, such as methylene chloride. The reaction mixture is stirred further at temperatures of 0° to +50° C. for some time, 10 min. to 20 hours depending on the batch size, in order to complete the reaction. The catalyst is then deactivated by adding water. The organic phase of the reaction mixture is separated off and, after drying, worked up by distillation.

When carrying out the process according to the invention in the gas phase, the reaction is carried out at temperatures of about 200° to 450° C. Catalysts used are the Friedel-Crafts catalysts such as $Al_2O_3 \cdot SiO_2$, $H_3PO_4 \cdot SiO_2$, $BF_3/\gamma Al_2O_3$ and acidic zeolites customarily used for gas phase alkylations of aromatic compounds.

The gas phase alkylation according to the invention is carried out as follows: the aromatic compounds (II) and aliphatic halogen compounds IIIa–c are brought into the gaseous state by heating in a suitable apparatus, for example a coil or falling film evaporator, and transferred to a suitable reactor for continuous gas phase processes, for example a tube bundle reactor, which contains the alkylation catalyst in solid form. The reaction mixture leaving the reactor is separated into liquid and gaseous products by condensation.

The pure substances are obtained by fractional distillation, it optionally being possible beforehand to remove hydrogen chloride by washing processes, for example with water.

The condensation reaction on which the process according to the invention is based proceeds in two stages:

Stage 1:

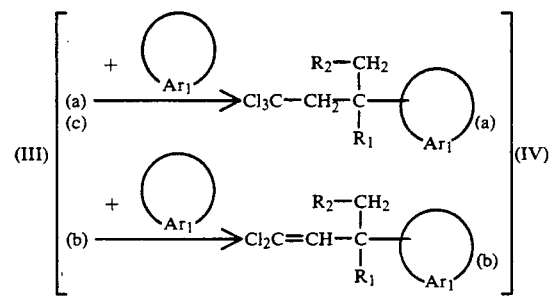

Stage 2:

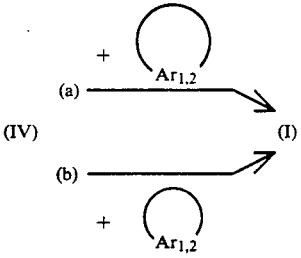

The process according to the invention can be carried out as one step or two steps, depending on whether it is wished to stop the alkylation reaction at the stage of the aralkyl compounds IVa or b or whether it is wished immediately to obtain the geminal diarylalkanes of the formula (I). The two stage procedure is preferably used for the preparation of geminal diarylalkanes of the formula (I) in which

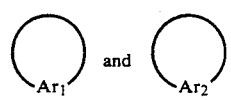

represent different aryl radicals.

In the two stage procedure, the condensation of the aromatic compounds in the first reaction stage with the aliphatic halogen compounds IIIa–c is carried out using weakly active Friedel-Crafts catalysts such as $ZnCl_2$, $ZnI_2$ or $SnCl_4$ and/or at low temperatures such as $-70°$ to $+10°$ C. and in short reaction times.

For the second stage, the condensation of the aralkyl compounds IVa or b with further aromatic compound II, stronger Friedel-Crafts catalysts such as $AlCl_3$ and higher temperatures such as $+25°$ C. to $+150°$ C. are used, as for the one stage procedure.

As already emphasized, the process according to the invention is suitable for the preparation of geminal diarylalkanes from all sorts of aromatic compounds. Suitable aromatic compounds are, for example, benzene, toluene, o-, m- and p-xylene, diphenylmethane, 2,2-diphenylpropane, diphenyl, 4-methyl-diphenyl, naphthalene, 1- and 2-methylnaphthalene, 2,3-dimethylnaphthalene, acenaphthene, chlorobenzene, bromobenzene, fluorobenzene, phenol, o-, m- and p-cresol, anisole, phenetole, diphenyl ether, thiophenol and diphenyl thioether.

Correspondingly, examples of optionally substituted aryl radicals

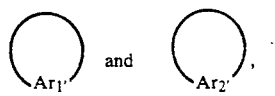

which may be mentioned are: phenyl, biphenyl, diphenylmethane, 2,2-diphenylpropane and naphthyl radicals optionally substituted by $C_1$–$C_4$-alkyl such as methyl, ethyl, isopropyl; hydroxyl; $C_1$–$C_4$-alkoxy such as methoxy and ethoxy; phenoxy; mercapto; $C_1$–$C_4$-alkylmercapto such as methylmercapto; phenylmercapto; and by halogen such as fluorine, chlorine or bromine, and in addition the acenaphthyl radical.

$C_1$–$C_{18}$-Alkyl radicals which may be mentioned for $R_1$ and $R_2$ are:

the methyl, ethyl, propyl, butyl, octyl, dodecyl, heptadecyl and octadecyl radical; suitable substituents for $R_2$ are, above all, halogen atoms such as chlorine atoms.

The geminal diarylalkanes of the formula (I) obtainable by the process according to the invention are mostly new. The new monomeric compounds are useful intermediates for the preparation of plastics, for example polyimides. The new geminal diarylalkanes, in particular the 2,2-diarylpropanes whose aryl groups are substituted by two vicinal methyl groups, open up the possibility of preparing new polyimides, which could not be prepared hitherto, with new interesting properties. The vicinal methyl groups of the aryl radicals are converted into carboxyl groups by oxidation, and the tetracarboxylic acids thus obtained are reacted with diamines to give polyimides.

The new oligomeric diarylalkanes are suitable as electrical insulating fluids and heat transfer fluids.

The invention therefore also relates to new geminal diarylalkanes; these correspond to the formula

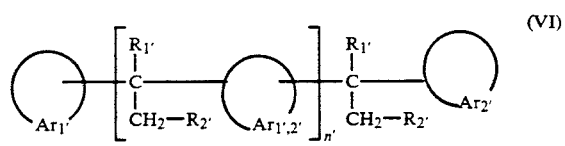

(VI)

in which, for the case in which n' is an integer from 1 to 5,

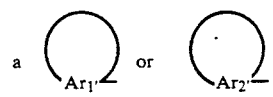

independently of one another, represent an optionally substituted aryl radical and

either denotes

a radical, with the proviso that when

is phenyl or hydroxyphenyl,

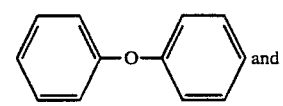

$R_1'$ represents hydrogen or a $C_1$–$C_{18}$-alkyl radical and $R_2'$ denotes hydrogen or an optionally substituted $C_1$–$C_{18}$-alkyl radical, and in which, for the case in which n' is zero,

represents

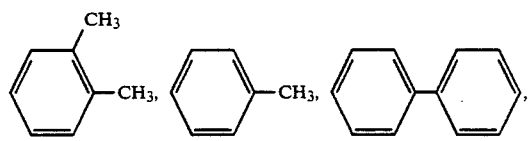

represents

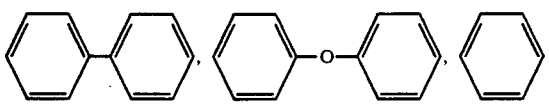

R₁' represents methyl and
R₂' represents hydrogen or methyl.

Examples of representatives of the new diarylalkanes of the formula (VI), when n'=0 in this, which may be mentioned are:

1-phenyl-1-xylyl-ethane, 2-phenyl-2-xylyl-propane, 2,2-bis-(4-chlorophenyl)-propane, 2,2-bis-(biphenyl)-propane, 2-biphenyl-2-xylyl-propane, 1-biphenyl-1-tolyl-ethane,2-biphenyl-2-tolyl-propane,2-biphenyl-2-phenyl-propane,2-phenyl-2-tolyl-propane, 2,2-bis-(p-phenoxy-phenyl)-propane, 2-phenyl-2-(p-phenoxy-phenyl)-propane and 2-(p-phenoxy-phenyl)-2-xylyl-propane.

The aralkyl compounds of the formulae (IVa and b) obtainable in the two stage implementation of the process according to the invention are also new; it has been found that these are not only intermediates for the preparation, in particular, of asymmetrical geminal diarylalkanes of the formula (I) but that they are also interesting intermediates for the preparation of plant protection agents and, for example, open up a new more favourable route for the preparation of known active compounds.

The invention therefore also relates to the aralkyl compounds of the formulae (IVa and b) in which

R₁ and R₂ have the meaning indicated under formula (I).

Examples of representatives of these new aralkyl compounds which may be mentioned are:

1,1,1-trichloro-3-methyl-3-phenyl-butane
1,1,1-trichloro-3-methyl-3-tolyl-butane
1,1,1-trichloro-3-methyl-3-xylyl-butane
1,1,1-trichloro-3-methyl-3-chlorophenyl-butane
1,1,1-trichloro-3-methyl-3-bromophenyl-butane
1,1,1-trichloro-3-methyl-3-fluorophenyl-butane
1,1,1-trichloro-3-methyl-3-ethoxyphenyl-butane
1,1,1-trichloro-3-methyl-3-hydroxyphenyl-butane
1,1,1-trichloro-3-methyl-3-mercaptophenyl-butane
1,1,1-trichloro-3-methyl-3-methylmercapto-phenyl-butane
1,1,1-trichloro-3-methyl-3-tolyl-butane
1,1,1-trichloro-3-methyl-3-xylyl-pentane
1,1,1-trichloro-3-methyl-3-chlorophenyl-pentane
1,1,1-trichloro-3-methyl-3-fluorophenyl-pentane
1,1,1-trichloro-3-methyl-3-ethoxyphenyl-pentane
1,1,1-trichloro-3,4-dimethyl-3-tolyl-pentane
1,1,1-trichloro-3,4-dimethyl-3-xylyl-pentane
1,1,1-trichloro-3,4-dimethyl-3-fluorophenyl-pentane
1,1,1-trichloro-3,4-dimethyl-3-ethoxyphenyl-pentane
1,1,1-trichloro-3-methyl-3-biphenyl-butane
1,1,1-trichloro-3-methyl-3-biphenyl-pentane
1,1,1-trichloro-3-methyl-3-naphthyl-butane
1,1,1-trichloro-3-methyl-3-dimethylnaphthyl-butane
1,1,1-trichloro-3-methyl-3-acenaphthyl-butane
1,1,1-trichloro-3-methyl-3-phenoxyphenyl-butane
1,1-dichloro-3-phenyl-butene
1,1-dichloro-3-tolyl-butene
1,1-dichloro-3-hydroxyphenyl-butene
1,1-dichloro-3-methoxyphenyl-butene
1,1-dichloro-3-fluorophenyl-butene
1,1-dichloro-3-cumyl-butene
1,1-dichloro-3-biphenyl-butene
1,1-dichloro-3-phenyl-pentene
1,1-dichloro-3-tolyl-pentene
1,1-dichloro-3-methoxyphenyl-pentene
1,1-dichloro-3-ethoxyphenyl-pentene
1,1-dichloro-3-hydroxyphenyl-pentene
1,1-dichloro-3-phenyl-heptene
1,1-dichloro-3-tolyl-undecene
1,1-dichloro-3-phenyl-heptadecene
1,1-dichloro-3-phenyl-nonadecene
1,1-dichloro-3-methyl-3-phenyl-butene
1,1-dichloro-3-methyl-3-tolyl-butene
1,1-dichloro-3-methyl-3-chlorophenyl-butene
1,1-dichloro-3-methyl-3-xylyl-butene
1,1-dichloro-3-methyl-3-ethoxyphenyl-butene
1,1-dichloro-3-methyl-3-hydroxyphenyl-butene
1,1-dichloro-3-methyl-3-tolyl-pentene
1,1-dichloro-3-methyl-3-ethoxyphenyl-pentene
1,1-dichloro-3-methyl-3-xylyl-pentene
1,1-dichloro-3,4-dimethyl-3-phenyl-pentene
1,1-dichloro-3,4-dimethyl-3-tolyl-pentene
1,1-dichloro-3,4-dimethyl-3-xylyl-pentene
1,1-dichloro-3,4-dimethyl-3-fluorophenyl-pentene
1,1-dichloro-3,4-dimethyl-3-ethoxyphenyl-pentene The significance of the compounds IVa and b as intermediates for the preparation of plant protection agents may be illustrated as exemplified by the preparation of insecticides of the type MTI 800 (see DE-OS (German Published Specification) 3,317,907). A multistage process is described for the preparation of these aromatic alkane derivatives which requires complicated reactions and the use of expensive reagents which can only be handled with difficulty on the industrial scale, such as Grignard compounds and LiAlH₄ (see DE-OS (German Published Specification) 3,317,908, and the reaction scheme on p. 62/63). With the aid of the aralkyl compounds of the formulae IVa and b according to the invention, not only the number of reaction steps can be substantially lowered, but the individual reactions can be carried out without difficulties on the industrial scale, as they only require simple reagents customarily used in chemical techniques.

That is to say that, with the aid of the aralkyl compounds of the formula IVa and b according to the invention, the active compounds described in DE-OS (German Published Specification) 3,317,908 can be prepared in a simplified, essentially more economical way.

EXAMPLE 1

25 g (0.12 mol) of 1,1,1,3-tetrachloro-3-methylbutane in 250 g (3.2 mol) of benzene are added in the course of 15 min with stirring and cooling at temperatures of 0° to 5° C. to a solution of 2.5 g (0.019 mol) of AlCl₃ in 10 ml of dichloromethane. The reaction mixture is stirred at 5° C. for 100 min. After adding 50 ml of water, the organic phase is separated off, dried and fractionally distilled.

268 g of crude product are obtained, which according to GC analysis contains 4.1% of vinylidene chloride.(=11 g=94.8% of theory). 20.4 g (=87% of theory) of 2,2-diphenyl-propane (b.p.: 89° C./0.1 mbar) are obtained by fractional distillation of the crude product.

EXAMPLE 2

500 g (2.38 mol) of 1,1,1,3-tetrachloro-3-methylbutane are added in the course of 10 min. with stirring and cooling at 0° C. to a solution of 20 g (0.15 mol) of $AlCl_3$ in 2,500 g (27 mol) of dry toluene. The reaction mixture is stirred at 0° C. for 60 min and, after adding 200 ml of water, the organic phase is separated off, dried using sodium sulphate and worked up by fractional distillation.

145 g (=72% of theory) of vinylidene chloride, 90 g of unreacted 1,1,1,3-tetrachloro-3-methyl-butane and 410 g (=94% of theory) of 2,2-di-tolyl-propane (isomer mixture; b.p.: 106°-115° C./0.1 mbar) are obtained. Content of p,p'-isomer of the isomer mixture: 65%.

EXAMPLE 3

100 g (0.48 mol) of 1,1,1,3-tetrachloro-3-methylbutane are added with stirring at room temperature to a solution of 2.5 g (0.015 mol) of anhydrous $FeCl_3$ in 1,400 g (15.2 mol) of anhydrous toluene. The reaction mixture is stirred at 50° to 60° C. for 60 min and then at reflux temperature for 180 min. After adding water, the organic phase is separated off, dried and worked up by distillation.

80.8 g (=73.5% of theory) of 1,1-dichloro-3-tolyl-3-methyl-but-1-ene are obtained (b.p.: 85°-89° C./0.2 mbar).

EXAMPLE 4

500 g (2.38 mol) of 1,1,1,3-tetrachloro-3-methylbutane are added with stirring and cooling at temperatures of 0° to 10° C. in the course of 30 min to a solution of 50 g (0.38 mol) of $AlCl_3$ in 5,000 g (44.6 mol) of dry chlorobenzene. The reaction mixture is stirred at 10° C. for a further 90 min. After adding 500 ml of water, the organic phase is separated off, washed with soda solution until neutral and dried using sodium sulphate.

The following are obtained in the fractional distillation: 4,750 g of precursor; it contains 4.5% (=213 g=92.6% of theory) of vinylidene chloride according to GC analysis; 532 g (=84.3% of theory) of 2,2-bis-(chlorophenyl)-propane (predominantly the p,p'-isomer) (b.p.: 160°-165° C./0.8 mbar) and 84 g ,(=14% of theory) of 1,1-dichloro-3-chlorophenyl-3-methyl-butene (predominantly the p,p'-isomer) (b.p.: 115°-118° C./0.3 mbar).

EXAMPLE 5

30 g (0.14 mol) of 1,1,1,3-tetrachloro-3-methylbutane are added with stirring to a solution of 2 g (0.015 mol) of $AlCl_3$, 462 g (3.0 mol) of diphenyl and 106 g (1.0 mol) of o-xylene in 450 ml of methylene chloride. The reaction mixture is stirred at 10° C. for a total of 20 hours, a further 2 g of $AlCl_3$ being additionally added after 5 and 7 hours in each case. After adding 50 ml of water, the organic phase is separated off and, after drying, worked up by distillation.

Unreacted o-xylene and diphenyl ar recovered. 13.8 g (=32% of theory) of a fraction of boiling range 210°-225° C./0.2 mbar consisting predominantly of 2-biphenyl-2-xylyl-propane and 15 g (=30% of theory) of a fraction of boiling range 225°-250° C./0.2 mbar consisting essentially of 2,2-bis-(biphenyl)-propane are obtained. m.p. of the 2,2-bis-(biphenyl)-propane purified by recrystallization from hexane: 138°-139° C.

EXAMPLE 6

30 g (0.14 mol) of 1,1,3-trichloro-but-1-ene are added in the course of 30 min at 0° C. with stirring and cooling to a solution of 2.8 g of $AlCl_3$ (0.02 mol) in 300 ml (3.0 mol) of dry benzene. The reaction mixture is stirred at 0° to 5° C. for a further 90 min. After adding 50 ml of water, the organic phase is separated off and worked up by fractional distillation.

27 g (=71% of theory) of 1,1-dichloro-3-phenyl-but-1-ene (b.p.: 73°-74° C./0.15 mbar) and 2.6 g (=7.6% of theory) of 1,1-bisphenyl-ethane (b.p.: 87°-89° C./0.1 mbar) are obtained.

EXAMPLE 7

The reaction was carried out as described in Example 6 with the difference that the reaction temperature was 25° C. and the reaction time 18 hours. The precursor (210 g) removed by distillation under normal pressure contains 5.9% (=13.4 g=91% of theory) of vinylidene chloride according to GC analysis. 18.2 g (=53% of theory) of 1,1-bisphenylethane (b.p.: 88°-90° C./0.1 mbar) are obtained in the subsequent vacuum distillation.

EXAMPLE 8

First 5 g of $AlCl_3$ and then 30 g of 1,1,1,3 -tetrachloro-3-methyl-butane are added with stirring and cooling to a solution of 500 g of diphenyl ether in 300 ml of dichloromethane. After stirring for 5 hours, 5 g of $AlCl_3$ are again added and the reaction mixture is warmed to 22° C. After a further reaction time of 10 hours, 200 ml of water are added dropwise and the phases are separated. The organic phase which has been dried using sodium sulphate is distilled.

33.3 g (=61% of theory) of 2,2-bis-(4-phenoxyphenyl)-propane (b.p.: 225°-230° C./0.6 mbar) are obtained.

EXAMPLE 9

1 g of $AlCl_3$ and 30 g of 1,1,1,3-tetrachloro-3-methylbutane are added at 0° C. to a solution of 154 g of biphenyl in 312 g of benzene. After stirring for 5 hours, a further 2 g of $AlCl_3$ are added and the reaction mixture is stirred at 20°-25° C. for a further 10 hours. After adding 50 ml of water, the phases are separated. The organic phase is worked up by distillation.

13.5 g of 2-biphenyl-2-phenyl-propane (b.p.: 190°-195° C./0.05 mbar) are obtained in addition to 2,2-diphenylpropane and 2,2-bis-(biphenyl)-propane.

EXAMPLE 10

300 g of 1,1,1,3-tetrachloro-3-methyl-butane are slowly added at 0° C. with stirring and cooling to a mixture of 2,400 ml of benzene, 600 ml of o-xylene and 12 g of $AlCl_3$. After stirring for 5 hours, the reaction is terminated by adding 250 ml of water. The organic phase is worked up by distillation. Vinylidene chloride, benzene and o-xylene are first removed by distillation under normal pressure; 290 g of unreacted 1,1,1,3-tetrachloro- 3-methyl-butane, 33 g of 2-phenyl-2-o-xylylpropane (boiling range: 130° C.-134° C./0.4 mbar) and 61 g of 2,2-bis-(o-xylyl)-propane (b.p.: 158° C.-160° C./0.2 mbar) are then obtained by vacuum distillation.

EXAMPLE 11

25 g of $AlCl_3$ are dissolved in 2,700 ml of anhydrous o-xylene with stirring. 270 g of 1,1,1,3-tetrachloro-3- methyl-butane are then added dropwise with stirring in the course of 15 minutes; the reaction mixture is then initially stirred at 0° C.-10° C. for one hour, then at 20° C. for a further hour. The reaction is terminated by adding 1,000 ml of water. The separated organic phase is worked up by distillation. In addition to vinylidene chloride and xylene. 305 g (=94% of theory) of 2,2-bis-(o-xylyl)-propane (b.p.: 152° C.-155° C./0.15 mbar) are obtained.

EXAMPLE 12 a) A solution of 235 g (=1.12 mol) of 1,1,1,3-tetrachloro-3-methyl-butane in 800 g (8.7 mol) of toluene is added with stirring and cooling at −50° C. in the course of 20 min. to a suspension of 40 g of AlCl$_3$ in 100 ml of dichloromethane. After stirring at −50° C. for 40 minutes, water is added to the reaction mixture and the organic phase is separated off. After washing and drying the organic phase, this is freed from solvent and excess toluene in a rotary evaporator. 299 g of crude product are obtained, which contains 82% (=245 g=82.5% of theory) of 1,1,1-trichloro-3-methyl-3-p-tolyl-butane according to GC analysis. The pure compound (b.p.: 89° C./0.04 mbar) is obtained by distillation of the crude product.

b) Use of the 1,1,1-trichloro-3-methyl-3-p-tolylbutane for the preparation of 1-[4-fluoro-3-phenoxyphenyl]-4-methyl-4-p-tolyl-pentane.

α) The crude product from stage a) is mixed, with vigorous stirring, with a solution of 300 g of sodium hydroxide in 240 ml of water with the addition of 3 g of tetrabutylammonium bromide and the mixture is heated to 100° C. with stirring for 20 hours. The reaction mixture is extracted with dichloromethane; the combined extracts are washed with dilute hydrochloric acid and, after drying, worked up by distillation. 140 g (=78.8% of theory) of 1-chloro-3-methyl-3-p-tolyl-butine (b.p.: 114°-115° C./20 mbar) are obtained.

β) A solution of 96.5 g (0.5 mol) of 1-chloro-3-methyl-p-tolyl-butine in 500 ml of absolute methanol is heated to reflux temperature with stirring for 72 hours after adding 90 g of activated zinc dust. The reaction mixture is then concentrated in a rotary evaporator; the residue is taken up using dilute hydrochloric acid and dichloromethane and the organic phase is separated off. The organic phase is worked up by distillation; 66 g (=83% of theory) of 3-methyl-3-p-tolyl-butine (b.p.: 90°-92° C./22 mbar) are obtained.

γ) A solution of 0.2 mol of butyllithium in hexane is added at −70° C. with stirring to a solution of 32 g (0.2 mol) of 3-methyl-3-p-tolyl-butine in 150 ml of absolute tetrahydrofuran and then a solution of 43.2 g (0.2 mol) of 4-fluoro-3-phenoxy-benzaldehyde in 100 ml of tetrahydrofuran is added at −30° C. The reaction mixture is warmed to room temperature and stirred at this temperature for 12 hours. The solvent is then removed in vacuo and the residue is taken up using water and dichloromethane. The organic phase is separated off and worked up by distillation. 72 g of crude product are obtained, which consists essentially of 1-[4-fluoro-3-phenoxyphenyl]-3-methyl-3-p-tolyl-pent-2-in-1-ol according to GC-MS analysis (by-product: 4-fluoro-3-phenoxyphenyl 3-methyl-3-p-tolyl-butin-1-yl ketone).

δ) The crude product is dissolved in 2,000 ml of methanol and the solution is hydrogenated at 80° C. and at a hydrogen pressure of 40 bar in a stirring autoclave after adding 7 g of Pd-C (5%). After separating off the Pd catalyst and concentrating the reaction solution in a rotary evaporator, 69 g of a crude product are obtained which contains 93% (=64.2 g=88.6% of theory) of 1-[4-fluoro-3-phenoxyphenyl]-4-methyl-4p-tolyl-pentane ($n_D^{20}$: 1.5629) according to GC-MS analysis.

EXAMPLE 13 a) A mixture of 61 g (0.5 mol) of phenetole and 105 g (0.5 mol) of 1,1,1,3-tetrachloro-3-methyl-butane is added slowly with stirring at 0° C. to a suspension of 66.5 g (0.5 mol) of AlCl$_3$ in 100 ml of dichloromethane. After stirring for 4 hours, 1,000 ml of water are added to the reaction mixture with ice-cooling. The mixture is extracted several times with dichloromethane and, after drying, the combined extracts are worked up by distillation. 30 g (=20% of theory) of 1,1,1-trichloro-3-p-ethoxyphenyl-3methyl-butane (b.p.: 145°-150° C./0.1 mbar) are obtained in addition to unreacted starting material.

b) Use of the 1,1,1-trichloro-3-p-ethoxyphenyl-3-methylbutane for the preparation of 1-[4-fluoro-3-phenoxy-phenyl]-4-[p-ethoxyphenyl]-4-methyl-pentane.

α) The mixture of 1,1,1-trichloro-3-p-ethoxyphenyl-3-methyl-butane obtained in step a), 25 g of potassium tert.-butoxide and 200 ml of dimethylformamide is heated at 85° C. with stirring for 12 hours. tert.-Butanol and dimethylformamide are then removed from the reaction mixture by vacuum distillation. The residue is taken up in water and dichloromethane and the organic phase is separated off. 20 g (=89% of theory) of 1-chloro-3-epoxyphenyl-3-methyl-butine (b.p.: 98°-100° C./0.7 mbar) are obtained by vacuum distillation of the organic phase.

β) 20 g of 1-chloro-3-ethoxyphenyl-3-methyl-butine are added to a suspension of 20 g of activated zinc powder in 120 ml of methanol. The mixture is heated at reflux temperature with stirring for 24 hours. The methanol is then removed by distillation, the residue is taken up in dilute hydrochloric acid and dichloromethane and the organic phase is separated off. Distillation of the organic phase yields 14 g (=83% of theory) of 3-[p-ethoxyphenyl]-3-methyl-1-butine (b.p.: 71°-73° C./0.01 mbar).

γ) 0.01 mol of a solution of butyllithium in hexane is added at −30° C. with stirring to 1.9 g (0.01 mol) of 3-[p-ethoxyphenyl]-3-methyl-1-butine in 10 ml of absolute tetrahydrofuran. After stirring for 3 hours, a solution of 2.2 g (0.01 mol) of 4-fluoro-3-phenoxy-benzaldehyde in 10 ml of tetrahydrofuran is added to the reaction mixture. The reaction mixture is warmed to room temperature and, after stirring at this temperature for 5 hours, water and dichloromethane (100 ml each) are added. The organic phase is separated off and concentrated in vacuo. 3.6 g of crude product are obtained, which contains 85% of 1-[4-fluoro-3-phenoxy-phenyl]-4-[p-ethoxyphenyl]-4-methyl-pent-1-in-1-ol (in addition to 7% of the corresponding ketone) according to GC-MS analysis. The crude product is catalytically hydrogenated under the conditions described in Example 8 δ). 3 g of 1-[4-fluoro-3-phenoxy-phenyl]-4-[p-ethoxyphenyl]-4-methyl-pentane (89% pure according to GC-MS analysis=2.7 g=69% of theory) are obtained. The compound is obtained pure by chromatography on silica gel ($n_D^{20}$: 1.5580).

What is claimed is:

1. A process for the preparation of a geminal diarylalkane of the formula

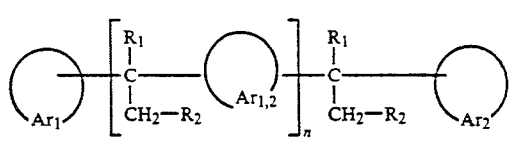 (I)

in which n is an integer from 0 to 5,

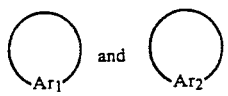 and independently of one another each is phenyl, biphenyl, diphenylmethane, 2,2-diphenylpropane or anyone of these radicals substituted by $C_1$–$C_4$-alkyl, hydroxyl, $C_1$–$C_4$-alkoxy, phenoxy, mercapto, $C_1$–$C_4$-alkylmercapto, phenylmercapto, halogen; or is acenaphthyl and

$R_1$ is hydrogen or $C_1$–$C_{18}$-alkyl and $R_2$ is hydrogen or $C_1$–$C_{18}$-alkyl or halogen substituted $C_1$–$C_{18}$-alkyl, which process comprises reacting at least one aromatic compound of the formula

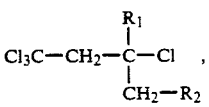 or 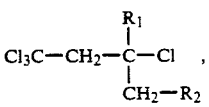 (II)

with at least one aliphatic halogen compound of the formula

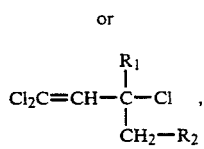 (IIIa)

or

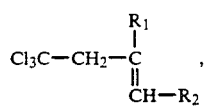 (IIIb)

or $$\begin{array}{c} R_1 \\ | \\ Cl_3C-CH_2-C \\ \| \\ CH-R_2 \end{array}$$ (IIIc)

in the presence of a Friedel-Crafts catalyst.

2. The process of claim 1, wherein the reaction is carried out in the liquid phase.

3. The process of claim 2, wherein the reaction is carried out at a temperature of $-50°$ to $+200°$ C.

4. The process of claim 2, wherein the reaction is carried out in an inert organic solvent or in an excess of a liquid aromatic compound of one of the formulae (II).

5. The process of claim 1 wherein for the preparation of a monomeric diarylalkane of the formula (I) in which n is zero, the aromatic compound of the formula (II) and the aliphatic halogen compound of formula (III) are employed in a molar ratio of 10 to 30:1.

* * * * *

UNITED STATES PATENT AND TRADEMARK OFFICE
CERTIFICATE OF CORRECTION

PATENT NO. : 5,136,114
DATED : August 4, 1992
INVENTOR(S) : Dieter Arlt It is certified that error appears in the above-identified patent and that said Letters Patent is hereby corrected as shown below:

Title Page   ABSTRACT:  Line 3 delete " 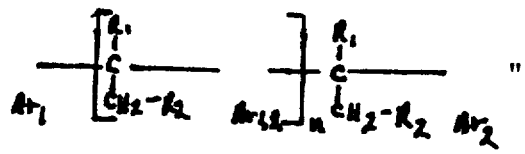 "

and substitute

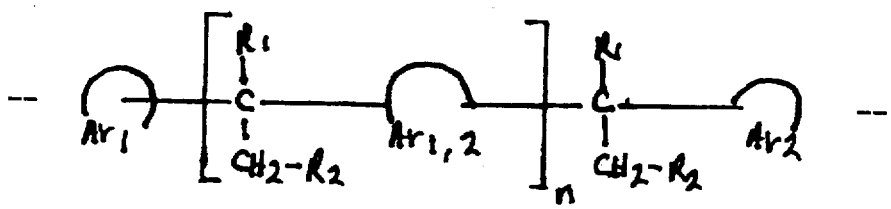

Signed and Sealed this

First Day of March, 1994

Attest:

BRUCE LEHMAN

Attesting Officer          Commissioner of Patents and Trademarks